United States Patent
Miyawaki et al.

(10) Patent No.: US 6,673,610 B2
(45) Date of Patent: Jan. 6, 2004

(54) METHOD FOR MUTAGENESIS (75) Inventors: Atsushi Miyawaki, Saitama (JP); Asako Sawano, Tokyo (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/920,922

(22) Filed: Aug. 2, 2001

(65) Prior Publication Data

US 2002/0083488 A1 Jun. 27, 2002

(30) Foreign Application Priority Data

Aug. 4, 2000 (JP) .................................... 2000-237166

(51) Int. Cl.$^7$ .................... C12N 15/00; C12Q 1/68; C12P 19/34; C07H 21/02; C07H 21/04
(52) U.S. Cl. ................... 435/440; 435/6; 435/91.2; 536/23.1; 536/24.3
(58) Field of Search ................... 435/440, 6, 91.2; 536/23.1, 24.3

(56) References Cited

U.S. PATENT DOCUMENTS

| | | | | |
|---|---|---|---|---|
| 5,354,670 | A | * | 10/1994 | Nickoloff et al. |
| 5,605,793 | A | * | 2/1997 | Stemmer |
| 5,789,166 | A | | 8/1998 | Bauer et al. |
| 5,811,238 | A | * | 9/1998 | Stemmer et al. |
| 5,932,419 | A | | 8/1999 | Bauer et al. |
| 5,939,250 | A | * | 8/1999 | Short |

OTHER PUBLICATIONS

Berger et al. Phoenix Mutagenesis : One–step reassembly of multiply cleaved plasmids with mixtures of mutant and wild–type fragments. Analytical Biochemistry 214 : 571–579 (1993).*
Hermes et al. A reliable method for random mutagenesis: the generation of mutant libraries using spiked oligodeoxyribonucleotide primers. Gene 84 : 143–151 (1989).*
Derbyshire et al. A simple and efficient procedure for saturation mutagenesis using mixed oligodeoxynucleotides Gene 46 : 145–152 (1986).*
Caldwell et al. Randomization of genes by PCR mutagenesis. PCR Methods and Applications 2 : 28–33 (1992).*
Wells et al. Cassette mutagenesis : an efficient method for generation of multiple mutations at defined sites. Gene 34 : 315–323 (1985).*
Smith M. In vitro mutagenesis. Ann. Rev. Genet. 19 : 423–462 (1985).*
Perlak F. Single step large scale site–directed in vitro mutagenesis using multiple oligonucleotides. Nucleic Acids Research 18 (24) : 7457–7458 (1990).*
Liao et al. A simple high–efficiency method for random murtagenesis of cloned genes using forced nucleotide misincorporation. Gene 88 : 107–111 (1990).*
Sarkar et al. The "Megaprimer" method of site–directed mutagenesis. BioTechniques 8 (4) :; 404–407 (1990).*

Picard et al. A rapid and efficient one–tube PCR–based mutagenesis technique using Pfu DNA polymerase. Nucleic Acids Research 22(13) : 2587–2591 (1994).*
Ito et al. A general method for introducing a series of mutations into cloned DNA using the polymerase chain reaction. Gene 102 (1) 67–70 (1991).*
Landt et al. A general method for rapid site–directed mutagenesis using the polymerase chain reaction. Gene 96 : 25–128 (1990).*
Ge et al. Simultaneous Introduction of multiple mutations using overlap extension PCR. BioTechniques 22 (1) : 28–30 (1997).
Amplification of closed circular DNA in vitro, Nucleic Acids Research, 1998, vol. 26, No. 4, Pages 1126–1127.
European Search Report.
XP–002179561; Approaches to DNA Mutagenesis: An Overview; Analytical Biochemistry, 254, Pgs. 157–178 (1997); Article No. aB9724B28.
XP–001019207; Two–Stage PCR Protocol Allowing Introduction of Multiple Mutations, Deletions and Insertions Using Quick–Change Site–Directed Mutagenesis; vol. 26, No. 4 (1999).
XP–002096735; An improved PCR–mutagenesis strategy for two–site mutagensis or sequence swapping between related genes; Nucleic Acids Research, 1998, vol. 26, No. 7 Pgs. 1848–1850.
XP–002179562; Directed evolution of green fluorescent protein by a new versatile PCR strategy for site–directed and semi–random mutagensis; Nucleic Acids Research, 2000, vol. 28, No. 16.
XP–002179563; Circularly permuted green fluorescent proteins engineered to sense $CA^{2+}$.
XP–001019204; Short Technical Reports; Integrations of PCR Fragments at Any Specific Site within Cloning Vectors without the Use of Restriction Enzymes and DNA Ligase; BioTechniques 31:88–92 (Jul. 2001).

* cited by examiner

Primary Examiner—Ethan Whisenant
(74) Attorney, Agent, or Firm—Fish & Richardson P.C.

(57) ABSTRACT

The present invention provides an entirely new method for mutagenesis, which is simple, speedy, economical, and widely-applicable.

A method for mutagenesis comprising steps of:
DNA synthesis in which primers which have mutations and a phosphorylated 5'-terminus are annealed to a template DNA and then subjected to an elongation reaction using a thermostable high-fidelity DNA polymerase, after which the phosphorylated 5'-terminus and the elongated terminus are ligated by means of a thermostable DNA ligase to synthesize a circular DNA containing said primers;
digestion in which at least DNAs other than the amplified circular DNA are digested into several fragments; and
double-stranded DNA synthesis in which, with the several fragments obtained in the above step of digestion as megaprimers, said megaprimers are annealed to said circular DNA synthesized in the above step of DNA synthesis, followed by an elongation reaction performed using said thermostable high-fidelity DNA polymerase.

12 Claims, 5 Drawing Sheets

METHOD FOR MUTAGENESIS

FIELD OF THE INVENTION

The present invention relates to an entirely new method for mutagenesis, which can be applied for introducing certain mutations at certain sites of a nucleotide sequence, or for introducing random mutations at certain sites of a nucleotide sequence.

BACKGROUND OF THE INVENTION

The method for site-directed mutagenesis is a powerful tool for producing mutants to assess the importance of specific amino acid residues in a protein's structure and function. As such method for site-directed mutagenesis, a variety of protocols have been established, including those using the polymerase chain reaction (PCR).

Among the PCR-based protocols, the Quik Change™ Site-Directed Mutagenesis Kit (Stratagene, La Jolla, Calif., USA) (referred to as "Quik Change method", hereinafter) is widely used. According to the protocol of said Quik Change method, a DNA containing mutations can be obtained through the following three steps of:
1) carrying out the PCR process by use of a pair of complementary primers designed to carry a mutation at a desired site;
2) digesting only the template DNAs (that carry no mutations) in the reaction solution; and
3) performing transformation by use of the DNA fragments which are not digested in the above step of digestion.

In particular, said Quik Change method utilizes, in the step of carrying out the PCR process, a supercoiled, double-stranded (ds) DNA plasmid as a template DNA, and a high-fidelity Pfu Turbo™ DNA polymerase as an enzyme. During the step of the PCR process, the pair of complementary primers is annealed to the dsDNA, followed by an elongation reaction so as to amplify DNA fragments that carry mutations and are nicked between the elongated terminus and the 5'-terminus of the primers.

Subsequently, in the Quik Change method, DpnI endonuclease is caused to act in the reaction solution to specifically cut fully- or hemi-methylated 5'-GATC-3' sequences. The in vitro synthesized and nicked plasmid DNA including the desired mutation is then transformed into *E coli*. As a result, the plasmid DNA that is nicked will be repaired in *E coli* and become circular.

Thus, according to the Quik Change method, it is possible to synthesize a DNA including a desired mutation at a desired site. However, the Quik Change method suffers from the following disadvantages:
1) multiple mutations can not be introduced at different relatively separated positions in a nucleotide sequence at the same time, i.e., in this method, it is possible to introduce multiple mutations only in a pair of complementary primers, whereas it is impossible to introduce multiple mutations at remote positions;
2) when introducing a mutation, a pair of synthetic complementary oligonucleotides primers is required, that is, this method requires two primers for introducing a mutation at one site; and
3) since it requires a pair of synthetic complementary oligonucleotides primers, it does not allow random mutagenesis at desired sites using degenerative primers.

The Quik Change method, due to the above problem 1), requires that the aforementioned 3 steps be repeated the number of times corresponding to the number of mutagenesis, when introducing mutations at multiple sites. Consequently, the Quik Change method takes a long time to introduce mutations at multiple sites, leading to an inconvenience of poor efficiency. Additionally, the Quik Change method, owing to the above problem 2), involves high cost in synthesizing or purchasing the pair of synthetic oligonucleotides primers. Moreover, the Quik Change method, due to the above problem 3), can not be used in experimental systems where certain amino acid residues in the analyte protein are mutated into a variety of other amino acids, thus limiting the experimental systems to which it is applicable.

SUMMARY OF THE INVENTION

Thus, in view of the problems of prior art mentioned above, an object of the present invention is to provide an entirely new method for mutagenesis, which method being simple, speedy, economical, and widely-applicable.

The method for mutagenesis according to the present invention, having achieved said object, comprises the following steps of:
a DNA synthesis in which one or more primers which have a nucleotide sequence containing at least one mutation and a phosphorylated 5'-terminus are annealed to a template DNA and then subjected to an elongation reaction using a thermostable high-fidelity DNA polymerase, after which the phosphorylated 5'-terminus and the elongated terminus are ligated by means of a thermostable DNA ligase to synthesize a circular DNA containing said primers;
a digestion in which said step of DNA synthesis is repeated several times to amplify the DNA containing said primers, after which at least the DNAs other than the amplified circular DNA are then digested into several fragments; and
a double-stranded DNA synthesis in which, with the several fragments obtained in the above step of digestion as megaprimers, said megaprimers are annealed to said circular DNA synthesized in the above step of DNA synthesis, followed by an elongation reaction performed using said thermostable high-fidelity DNA polymerase.

EMBODIMENT OF THE PRESENT INVENTION

The method of mutagenesis according to the present invention will be described below in detail with reference to the attached drawings. Following examples will illustrate a method for introducing mutations at certain sites to a gene encoding the enhanced green fluorescent protein (referred to as EGFP hereinafter) which is made by altering the green fluorescent protein (GFP) produced by Aequorea. The method for mutagenesis according to the present invention is a method that is applicable not only for introducing mutations to said gene but to any genes.

Figure 1:
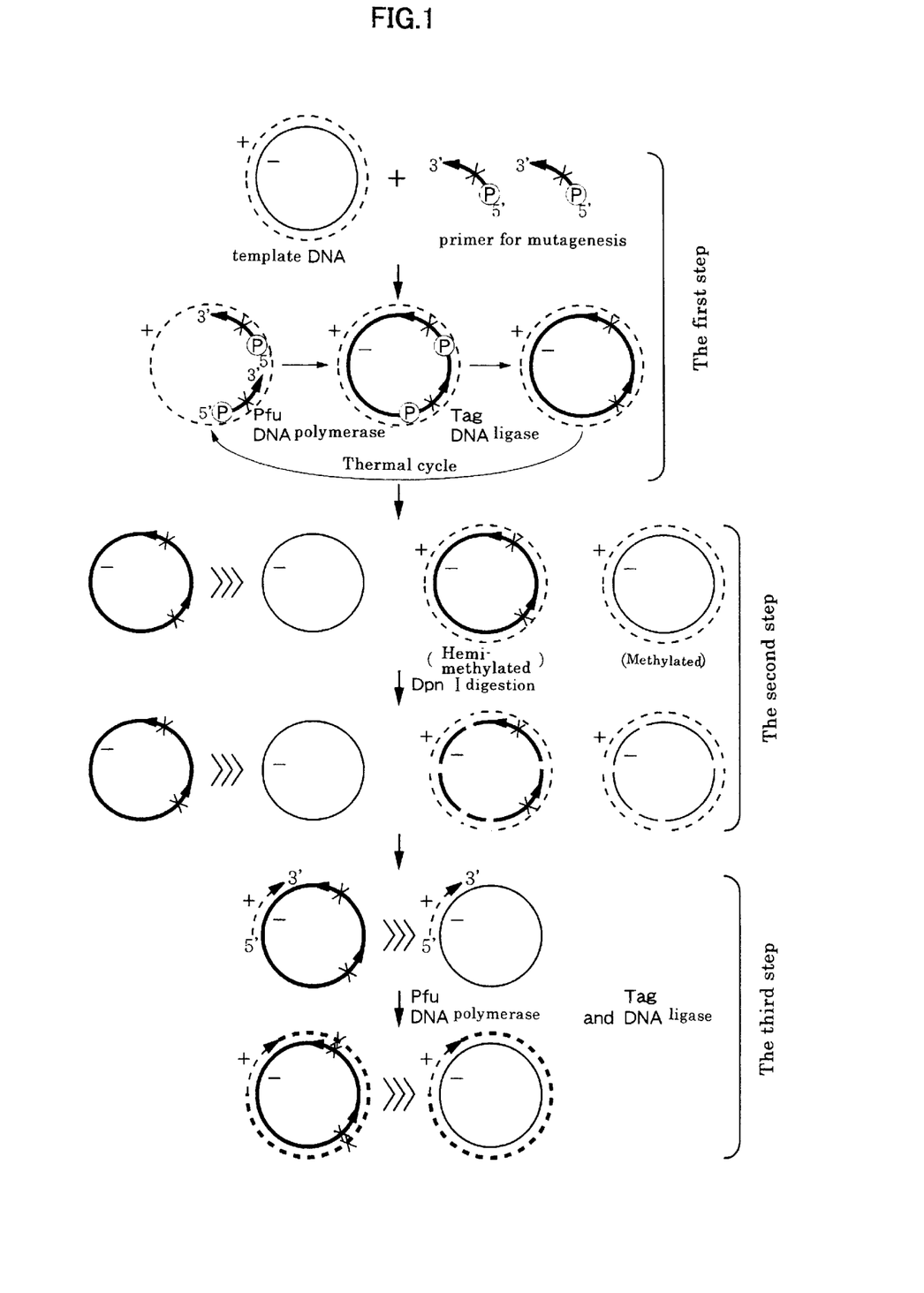
FIG. 1 is an overview illustrating the protocol of a method for mutagenesis according to the present invention.

The gene encoding said EGFP (SEQ ID NO.1) used herein is a gene which is changed in codon usage as compared with the gene encoding GFP (SEQ ID NO.3), and enhanced in expression within a host by adding a codon encoding valine between the first methionine and the second serine. EGFP (whose amino acid sequence is shown in SEQ ID NO.2) is made by replacing phenylalanine at position 64 in GFP (whose amino acid sequence is shown in SEQ ID NO.4) by leucine (at position 65 in EGFP) and serine at position 65 by threonine (at position 66 in EGFP). In the present specification, for indicating the position of an amino acid, all of the numerical values should be construed as those numbered on the basis of the amino acid sequence of GFP. Thus, for example "tyrosine at position 66 in EGFP" means the amino acid at position 67 in SEQ ID NO.2. In the present method, as shown in FIG. 1, mutations are introduced in a gene encoding EGFP through the first step of carrying out "synthesis of a mutated strand", the second step of carrying out "digestion with of DpnI" and the third step of carrying out "synthesis of a complementary strand by use of megaprimers".

(1) "Synthesis of a Mutated Strand"

First of all, primers for mutagenesis are prepared to introduce mutations at certain sites in the nucleotide sequence encoding known EGFP (SEQ ID NO.1). As the present method allows multiple mutations to be introduced at a time, the primers for mutagenesis are prepared in a number corresponding to the number of sites at which mutations are introduced.

These primers for mutagenesis are designed on the basis of SEQ ID NO.1 and at the same time are designed as those replacing certain bases in SEQ ID NO.1. The primers for mutagenesis are not limited to those replacing a single base and may be those replacing several bases. In this case, the primers for mutagenesis are designed such that they can be annealed to a plasmid containing a gene encoding EGFP.

The 5'-termini of these primers for mutagenesis have been phosphorylated using, for example, T4 polynucleotide kinase. Here, the enzyme that phosphorylates the 5'-termini of these primers for mutagenesis (after-mentioned Pri-1 or Pri-2), being not limited to T4 polynucleotide kinase, may include any enzymes capable of phosphorylating the 5'-termini of the primers.

Specifically, as a primer for mutagenesis, the following may be given by way of example: Pri-1 (5'-GCACTGCACGCCCAGGTCAGGGTGGT-3': SEQ ID NO.5) for mutating tyrosine (Y) at position 66 into tryptophan (W) and Pri-2 (5'-GGGCGGACTGGTAGCTC AGGTAGTGG-3': SEQ ID NO.6) for mutating threonine (T) at position 203 into tyrosine (Y).

In addition, a plasmid containing genes encoding EGFP is prepared. As such plasmid, for example, pRSET$_B$ (manufactured by Invitrogen Co.) having a T7 expression system may be used. At this time, a well-known approach can be used to construct pRSET$_B$ (pRSET$_B$/EGFP) containing genes encoding EGFP. The plasmids are normally methylated and the pRSET$_B$/EGFP used here is also methylated.

When synthesizing the mutated strand, a PCR process is carried out that uses these primers for mutagenesis (Pri-1 and Pri-2) and the relevant plasmid (pRSET$_B$/EGFP). In this process, a thermostable high-fidelity DNA polymerase is used in the elongation reaction from the primers for mutagenesis using a plasmid as a template. This thermostable high-fidelity DNA polymerase is that having about 10 times higher fidelity than other thermostable DNA polymerases such as TaqDNA polymerase, and capable of synthesizing a complementary strand for the template DNA substantially without mistake, for it has practically no activity to add excessively on the order of one base to the 3'-terminus of elongated strand. As a thermostable high-fidelity DNA polymerase, Pfu DNA polymerase (manufactured by Stratagene Co., La Jolla, Calif.) may be used. The thermostable high-fidelity DNA polymerase is not limited to Pfu DNA polymerase and may include any thermostable high-fidelity DNA polymerase as long as it has a high-fidelity and practically no activity to add excessively on the order of one base to the 3'-terminus of elongated strand.

In the PCR process, after the elongation reaction using the thermostable high-fidelity DNA polymerase, the 5'-terminus of a primer for mutagenesis and the 3'-terminus of an elongated DNA strand are ligated with a thermostable DNA ligase. As the thermostable DNA ligase, while not being specially limited, for example Taq ligase (New England Biolabs) may be used. In the present method, phosphorylation of the 5'-termini of the primers for mutagenesis allows the ligation as described above to be achieved.

The thermal cycler in said PCR process was programmed as follows: pre-incubation at 65° C. for 5 min allowing Taq DNA ligase to repair any nicks in the template DNA; initial denaturation at 95° C. for 2 min; 18 cycles, each cycle consisting of DNA denaturation at 95° C. for 30 sec, annealing reaction at 55° C. for 30 sec and elongation and ligation reaction at 65° C. for 7 min; and finally, post-incubation at 75° C. for 7 min. In this program, the time for the elongation and ligation reaction at 65° C. may be set longer to complete the ligation by means of Taq DNA ligase.

A program such as that described above enables to amplify only the single-stranded plasmid DNA containing a mutated EGFP gene made by introducing mutations that the primers for mutagenesis carry into a gene encoding EGFP. Specifically, the base sequence of a mutated EGFP gene synthesized using Pri-1 and Pri-2 as the primers for mutagenesis is shown in SEQ ID NO.8.

The final reaction solution of said PCR process comprises a single-stranded plasmid DNA containing the mutated EGFP gene, a single-stranded DNA derived from the plasmid being a template, a double-stranded plasmid being a template, and a double-stranded DNA made by annealing the single-stranded plasmid DNA containing the mutated EGFP gene and the single-stranded DNA derived from the plasmid being a template.

(2) "Digestion with DpnI"

In this step, at least an enzyme that digests DNA other than the single-stranded DNA containing the mutated EGFP gene is added to the reaction solution obtained as described above, to digest and remove only certain DNAs. As way of example, enzymes that can be used in this step include DpnI that recognizes and cuts certain nucleotide sequences (5'-G$^{m6}$ATC-3').

When DpnI is added to the reaction solution, it will selectively cut the methylated plasmid (pRSET$_B$/EGFP) remaining in the solution, and the hemi-methylated double-stranded DNA, made by annealing the single-stranded plasmid DNA containing the mutated EGFP gene and the single-stranded DNA derived from the plasmid being a template, remaining in the solution.

As a result, in the reaction solution, there exist as circular DNAs only the single-stranded DNA containing the mutated EGFP gene and a trace of the single-stranded DNA derived of plasmid being a template.

(3) "Synthesis of Complementary Strand by Use of Megaprimers"

In this step, the DNA fragments cut in the above step (2) are used as megaprimers and the single-stranded plasmid DNA containing the mutated EGFP gene is used as a template to synthesize a double-stranded DNA. Namely, in this reaction, the DNA fragments cut by DpnI are denatured to make single-stranded DNA fragments, while the single-stranded DNA fragments are annealed to the single-stranded plasmid DNA containing the mutated EGFP, and then an elongation reaction is performed using said single-stranded DNA fragments as megaprimers. This results in the synthesis of a nucleotide sequence complementary to the single-stranded plasmid DNA containing the mutated EGFP gene, so as to construct a double-stranded plasmid DNA containing EGFP genes in which mutations are introduced at desired sites.

Specifically, the megaprimers are denatured at 95° C. for 30 sec to become single-stranded, after which 2 cycles are carried out, each cycle consisting of thermal denaturation at 95° C. for 30 sec, annealing at 55° C. for 1 min and elongation reaction at 70° C. for 7 min, to synthesize a double-stranded DNA.

The DNA fragments obtained by treatment with DpnI include those containing wild-type bases present before the introduction of mutations. When using, as megaprimers, DNA fragments in which the sites to introduce mutations are wild-type nucleotide sequences, mutations will not be introduced into the synthesized complementary strand. Therefore, in this step, a large amount of an auxiliary primer is added in order to synthesize the double-stranded DNA in such a state that annealing of the relevant DNA fragment is prevented.

As an auxiliary primer, T7 primer can be used, which is complementary to the sequence present in the vicinity of the cloning site of the EGFP gene. Addition of T7 primer to the reaction solution allows the T7 primer to anneal preferentially, thus preventing the annealing of the DNA fragments in which the sites to introduce mutations are wild-type nucleotide sequences.

In this step, it is also possible to utilize Pfu DNA polymerase, Taq DNA ligase, dNTPs and NAD carried over from the PCR in the above step (1). Namely, in the present method, since the reaction can be carried out in the same reaction solution as used in the above steps (1) and (2) and continuously after these steps, the desired double-stranded plasmid DNA can be synthesized without going through a complex process such as purification of DNA fragments.

As seen from the above, the steps (1), (2) and (3) together make it possible to construct the double-stranded plasmid containing the mutated EGFP gene made by introducing mutations at certain sites in the EGFP gene. Further, certain cells are transformed using the reaction solution containing the relevant double-stranded plasmid to obtain transformed cells comprising plasmid containing the mutated EGFP gene.

The cells that can be used herein include any of the following: cells such as bacteria like *E. coli* and *Bacillus subtilis*, yeast cells, animal cells, insect cells and plant cells etc. The cells may be appropriately selected depending on the origin of the gene in which mutation is introduced or on the plasmid which is used. Also, in said transformation, any of the generally used approaches may be applied, for example, that using competent cells, that applying an electric pulse, or the like.

The mutated gene can be expressed by culturing the resulting transformed cells. For example, in the case of using pRSET$_B$/EGFP as a template DNA, *E. coli* JM109(DE3) is transformed and isopropyl β-D-thiogalactoside (IPTG) is added in the medium so as to induce expression of mutated EGFP.

Mutated protein, which is expressed in the transformed cells, can be purified by subjecting it to any of the protein purification processes that are generally used. For purifying the mutated protein, one may use, for example, affinity chromatography, gel filtration or the like.

However, in the above step (1) "synthesis of a mutated strand", the method for mutagenesis according to the present invention is not limited to those using multiple primers for mutagenesis, but also include those using degenerative primers to introduce random mutations into certain nucleotide sequences. The following example will illustrate a method wherein degenerative primers are used to mutate randomly amino acids at certain sites in ECFP (enhanced cyan fluorescent protein obtained by altering cyan fluorescent protein which is produced by Aequorea).

In this case, for example, as a degenerative primer, a degenerative primer Pri-3 (5'-GCGGACTGNNNGC TCAGGTAG-3': SEQ ID NO.7) is synthesized for mutating randomly threonine (T) at position 203 in the EGFP amino acid sequence. Here, "N" in the nucleotide sequence of Pri-3 (SEQ ID NO.7) means A, G, C or T, and can be synthesized by use of a nucleoside phosphoramidite containing A, G, C and T at equimolar concentrations.

In the above step (1) "synthesis of a mutated strand", Pri-3 can be used to construct a variety of mutated ECFP genes in which threonine (T) at position 203 in EGFP is randomly mutated.

EXAMPLES

The present invention will be described in more detail in the following examples, which, however, do not limit in any way the technical scope of the invention.

Example 1

1) Preparation of Primers for Mutagenesis and Template Plasmid DNA

In this example, tyrosine (Y) at position 66 is mutated into triptophan (W) and threonine (T) at position 203 into tyrosine (Y). As the primers for mutagenesis, Pri-1 (5'-GCACTGCACGCCCCAGGTCAGGGTGGT-3': SEQ ID NO.5) for mutating tyrosine (Y) at position 66 into triptophan (W) and Pri-2 (5'-GGGCGGACTGGTAGCTC AGGTAGTGG-3' SEQ ID NO.6) for mutating threonine (T) at position 203 into tyrosine (Y) were designed and synthesized. The 5'-termini of said Pri-1 and Pri-2 were phosphorylated respectively with T4 polynucleotide kinase.

To prepare a template plasmid DNA, the EGFP gene was cloned into a plasmid vector pRSET$_B$ (manufactured by Invitrogen Co.). The template plasmid DNA used hereafter is referred to as "pRSET$_B$/EGFP".

2) Synthesis of a Mutated Strand

50 µl of a reaction solution was prepared to carry out PCR:

| | |
|---|---|
| pRSET$_B$/EGFP | 50 ng |
| Pri-1 | 14 pmol |
| Pri-2 | 14 pmol |
| dNTPs | 10 nmol |
| Pfu DNA polymerase | 2.5 U |
| Taq DNA ligase | 20 U |

The Pfu DNA polymerase is that manufactured by Stratagene Co., and dissolved in a 0.5×Pfu polymerase reaction buffer. In addition, the Taq DNA ligase is that manufactured by New England Biolabs Co., and dissolved in a 0.5×Taq DNA ligase buffer containing 50 nmol of NAD.

The thermal cycler was programmed as follows: pre-incubation at 65° C. for 5 min allowing Taq DNA ligase to repair any nicks in the template DNA; initial denaturation at 95° C. for 2 min; 18 cycles, each cycle consisting of DNA denaturation at 95° C. for 30 sec, annealing reaction at 55° C. for 30 sec and elongation and ligation reaction at 65° C. for 7 min; and finally, post-incubation at 75° C. for 7 min.

3) Digestion with DpnI

DpnI was used under the following conditions to digest selectively the methylated or hemi-methylated plasmid DNAs. Namely, 1 µl (20 U) of DpnI (manufactured by New England BioLabs Co.) was added to 50 µl of the reaction solution after the above PCR process. This solution was then incubated at 37° C. for 1 hour.

DpnI is an endonuclease which recognizes (5'-G$^{m6}$ATC-3') to cut double-stranded DNAs. This DpnI completely cuts the plasmid pRSET$_B$/EGFP of 3672 bp to produce 23 DNA fragments of 6, 8, 11, 12, 17, 18, 24, 31, 36, 38, 46, 47, 75, 78, 105, 133, 148, 160, 258, 341, 506, 740, and 789 base pairs.

4) Synthesis of Complementary Strand by Use of Megaprimers

51 µl of the reaction solution after digestion by DpnI was used to synthesize a complementary strand for the mutation strand synthesized in the above step 2). That is, 51 µl of the reaction solution was denatured at 95° C. for 30 sec, after which 2 cycles at 95° C. for 30 sec, 55° C. for 1 min, and 70° C. for 7 min were carried out.

At this time, some of the 23 DNA fragments obtained in the above step 3) served as megaprimers.

5) Transformation and Expression of Mutated EGFP

2 µl of the sample after the reaction in the above step 4) was used to transform E. coli competent cell (JM109(DE3)) according to Ca$^{2+}$ coprecipitation. Then, the transformed E. coli was cultured at 37° C. in a LB solid medium containing 100 µg/ml ampicillin. Thereafter, grown single colonies were picked up and transferred to 2 ml of a LB liquid media containing 100 µg/ml ampicillin, which was cultured at 37° C. overnight to grow.

The mutated EGFP was expressed using the T7 expression system (pRSET$_B$/JM109(DE3)). Namely, a 100-fold dilution of the culture was prepared and grown at room temperature until said culture reached a density of approximately OD$_{600}$=0.5, and then expression of the mutated EGFP was induced by isopropyl β-D-thiogalactoside (IPTG) at a final concentration of 0.2 mM, followed by further culturing for 18 hours. The resultant cells were lysed by means of a French press, and the polyhistidine tagged proteins were purified from the cleared lysates using a nicke-chelate column (manufactured by Qiagen Co.). In addition, the protein samples in the eluates (100 mM imidazole, 50 mM Tris/Cl pH 7.5, 300 mM NaCl) were concentrated by Centricon 10 (Amicon) and were further purified by gel filtration.

6) Results

1. It was confirmed that mutations were introduced simultaneously at two sites in the resultant proteins by measuring the excitation wavelength and emission length of said proteins, and comparing them with those of existing proteins (such as wild-type EGFP).

Figure 2:
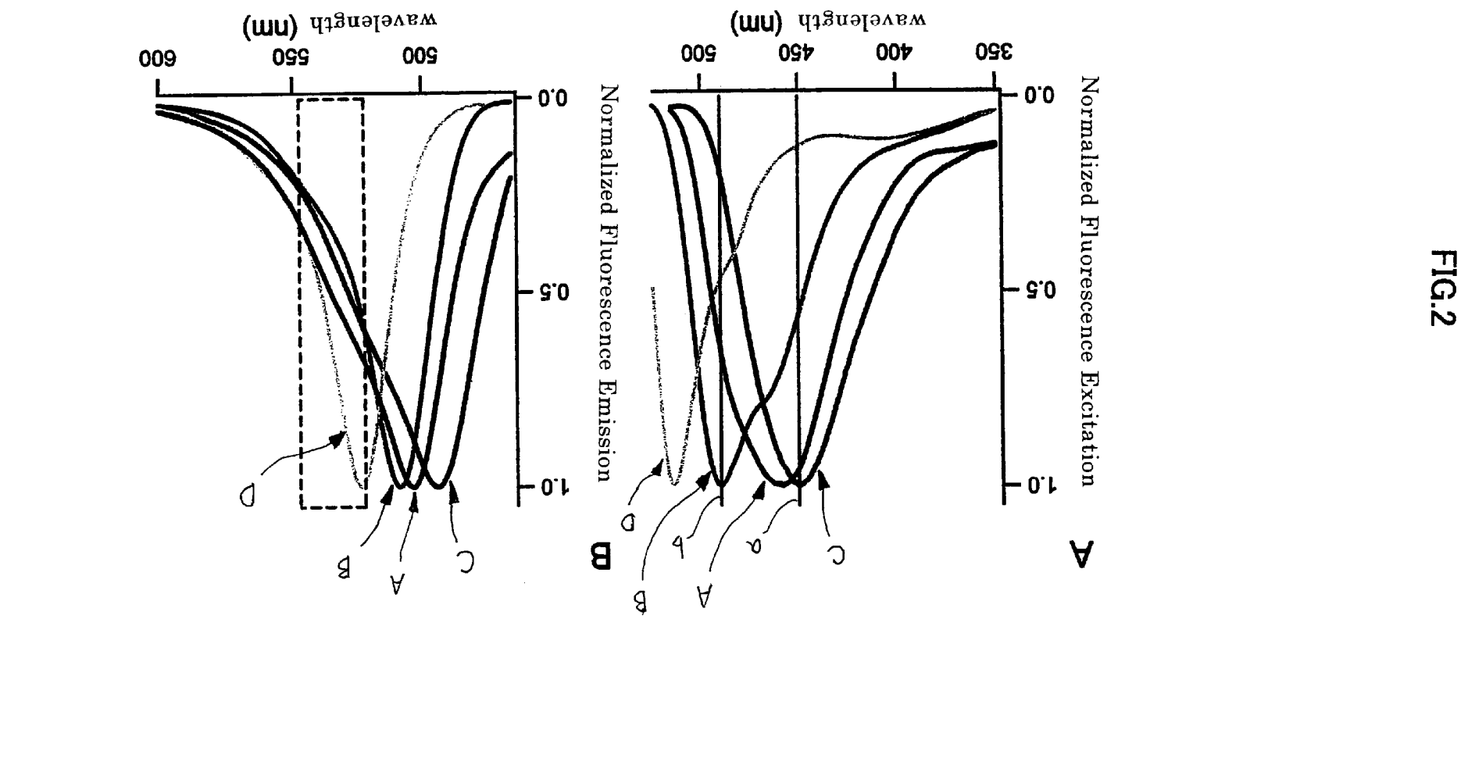
FIG. 2 shows the fluorescence excitation (A) and emission (B) spectra of EGFP, ECFP, EYFP and EGFP-Y66W/T203Y.

In FIG. 2(A), Curve A represents the excitation wavelength measured and normalized on the resultant proteins. In FIG. 2(B), Curve A represents the emission wavelength measured and normalized on the resultant proteins. Further, FIGS. 2(A) and (B) also show, for the purpose of comparison, the excitation and emission wavelengths on the wild-type EGFP-Y66W made by mutating tyrosine at position 66 into triptophan and the wild-type EGFP-T203Y made by mutating threonine at position 203 into tyrosine. In FIGS. 2(A) and (B), Curves B, C and D represent the wild-type EGFP, EGFP-Y66W and EGFP-T203Y, respectively.

As shown in FIGS. 2(A) and (B), it is found that the proteins in which mutations were introduced by the aforementioned method have an excitation wavelength peak at 458 nm and an emission wavelength peak at 504 nm. On the other hand, the wild-type EGFP has an excitation wavelength peak at 488 nm and an emission wavelength peak at 509 nm. EGFP-Y66W, producing a new chromophore containing indole by replacing tyrosine at position 66 by triptophan, has an excitation wavelength peak at 450 nm and an emission wavelength peak at 494 nm. EGFP-T203Y, producing a π-π interaction with tyrosine at position 66 by replacing threonine at position 203 by tyrosine, has an excitation wavelength peak at 514 nm and an emission wavelength peak at 524 nm.

The resultant proteins, being made by mutating tyrosine at position 66 into triptophan and mutating threonine at position 203 into tyrosine (EGFP-Y66W/T203Y), produce said π-π interaction and said chromophore containing indole, thus present a cyan-green luminescent color.

2. On the other hand, the mutation introduction rate is calculated by measuring the fluorescence of the colonies grown on the LB solid media containing ampicillin. Spectral properties of the relevant colonies were measured using a fluorescence image analysis system, which was adapted on the basis of the report by Baird et al. (Baird, G. S., Zacharias, D. A. and Tsien, R. Y. (1999) Proc. Natl. Acad. Sci. USA, 96, 11241–11246). In said image analysis system, the colonies grown on the LB plate (diameter of 9 cm) were excited by means of a 150 W xenon lamp. The excitation wavelength can be selected by a diffraction grating monochrometer (CT-10, manufactured by JASCO Co.). Specifically, the excitation wavelengths selected by said diffraction grating monochrometer are set to be 450 nm and 490 nm (indicated by the straight lines a and b in FIG. 2(A)).

Moreover, in this system, a pair of optical fibers (1 m) was used in order to illuminate the entire LB plate evenly. The fluorescence images from the colonies were collected through an interference band-pass filter (535DF25, 1 inch in diameter, manufactured by Omega Co.) into a lens (AF NIKKOR, manufactured by Nikon Co.). The images were captured by a SenSys cooled CCD camera (manufactured by Photometrics Co.) and analyzed using MetaMorph 3.0 software (manufactured by Universal Imaging Co., West Chester; Pa.). Specifically, the ratio image was obtained by dividing the 490 nm image by the 450 nm image. As expected from their excitation spectra shown in FIG. 2(A), the ratio values were as follows: EGFP-T203Y>wild-type EGFP>EGFP-Y66W/T203Y>EGFP-Y66W.

At this time, when comparing with the interference band-pass filter, use of the diffraction grating monochrometer permitted us to change and select excitation wavelengths of very narrow width. Thus, in this system, the excitation using said monochrometer enabled to definitely distinguish the wild-type EGFP, EGFP-T203Y, EGFP-Y66W and EGFP-Y66W/T203Y respectively, each of which presented close excitation spectra.

As a result, out of 42 colonies grown on the LB plate containing ampicillin, 32 of them showed cyan-green fluorescence (EGFP-Y66W/T203Y), and the efficiency of simultaneous mutagenesis at 2 sites was calculated to be 76%. The rest of the colonies were as follows: 4 showed yellow fluorescence (EGFP-T203Y); 4 showed cyan fluorescence (EGFP-Y66W); and 2 showed green fluorescence (wild-type EGFP). There were no non-fluorescent colonies.

Further, the experiment described above was repeated 4 times so as to calculate the rate of colonies showing cyan-green fluorescence, i.e., the efficiency of simultaneous mutagenesis at 2 sites. As a result, (number of colonies showing cyan-green fluorescence)/(total number of colonies) was 21/30, 42/50, 50/72 and 32/40, respectively and the efficiency of simultaneous mutagenesis at 2 sites was found to be 75.8%±4.2% (n=5).

Also, by DNA sequencing of the plasmid purified from the colonies showing cyan-green fluorescence, it was found that there were no mutations introduced other than at the sites of Pri-1 and Pri-2.

Moreover, out of 23 DNA fragments serving as megaprimers in the step 4), the sense strands of 506 bp and 148 bp contain a region encoding the amino acid residue 66 and a region encoding the amino acid residue 203, respectively. For this reason, it is preferable that these DNA fragments of 506 bp and 148 bp do not serve as megaprimers. In the present example, addition of a common sense-primer (T7 primer 14 pmol) that anneals outside the cloning site after DpnI digestion, enabling prevention of the annealing of the DNA fragments of 506 bp and 148 bp, can increase the efficiency of the mutagenesis to over 90%. Specifically, out of 200 colonies, 196 showed cyan-green fluorescence.

Example 2

In this example, a degenerative primer was used to mutate randomly threonine (T) at position 203 in the ECFP amino acid sequence. As the primer for mutagenesis, a degenerative primer Pri-3 (5'-GCGGACTGNNNGCTCAGGTAG-3': SEQ ID NO.7) was synthesized to mutate randomly threonine (T) at position 203, wherein "N" in the nucleotide sequence of Pri-3 (SEQ ID NO.7) means A, G, C or T. Then, the 5'-termini of these Pri-3 were respectively phosphorylated with T4 polynucleotido kinase.

As the template plasmid DNA, an ECFP gene was cloned into a plasmid vector pRSET$_B$ (manufactured by Invitrogen). Hereafter the template plasmid DNA used is "pRSET$_B$/ECFP". This ECFP gene has additional substitutions (N146I, M153T, V163A and N164H) to facilitate folding and maturation of the proteins, with tyrosine at position 66 being replaced by triptophan (Y66W).

For Example 2, the same experiment as in Example 1 was carried out, except that Pri-3 was used as the degenerative primer and pRSET$_B$/ECFP was used as the template DNA.
1) Results In this example, after the transformation carried out as described in Example 1, the transformed *E. coli* cell was grown on a LB plate containing ampicillin. 62 clones were randomly picked up and sequenced. As a result, 28 clones among them were found to be introduced mutations with threonine at position 203 being replaced by K, N, H, R or L and they produced non-fluorescent proteins. On the other hand, 34 clones produced fluorescent proteins, of which 23 contained mutants with threonine at position 203 was replaced by P, V, I, W, F, S, C or Y In particular, a remarkable change in spectrum was observed in the clone in which threonine at position 203 was mutated into tyrosine. This mutation is referred to as ECGFP (enhanced cyan-green fluorescent protein) because its overall excitation and emission spectra were intermediate between those of ECFP and EGFP. The amino acid sequence of ECGFP is shown in SEQ ID NO.9.

Figure 3:
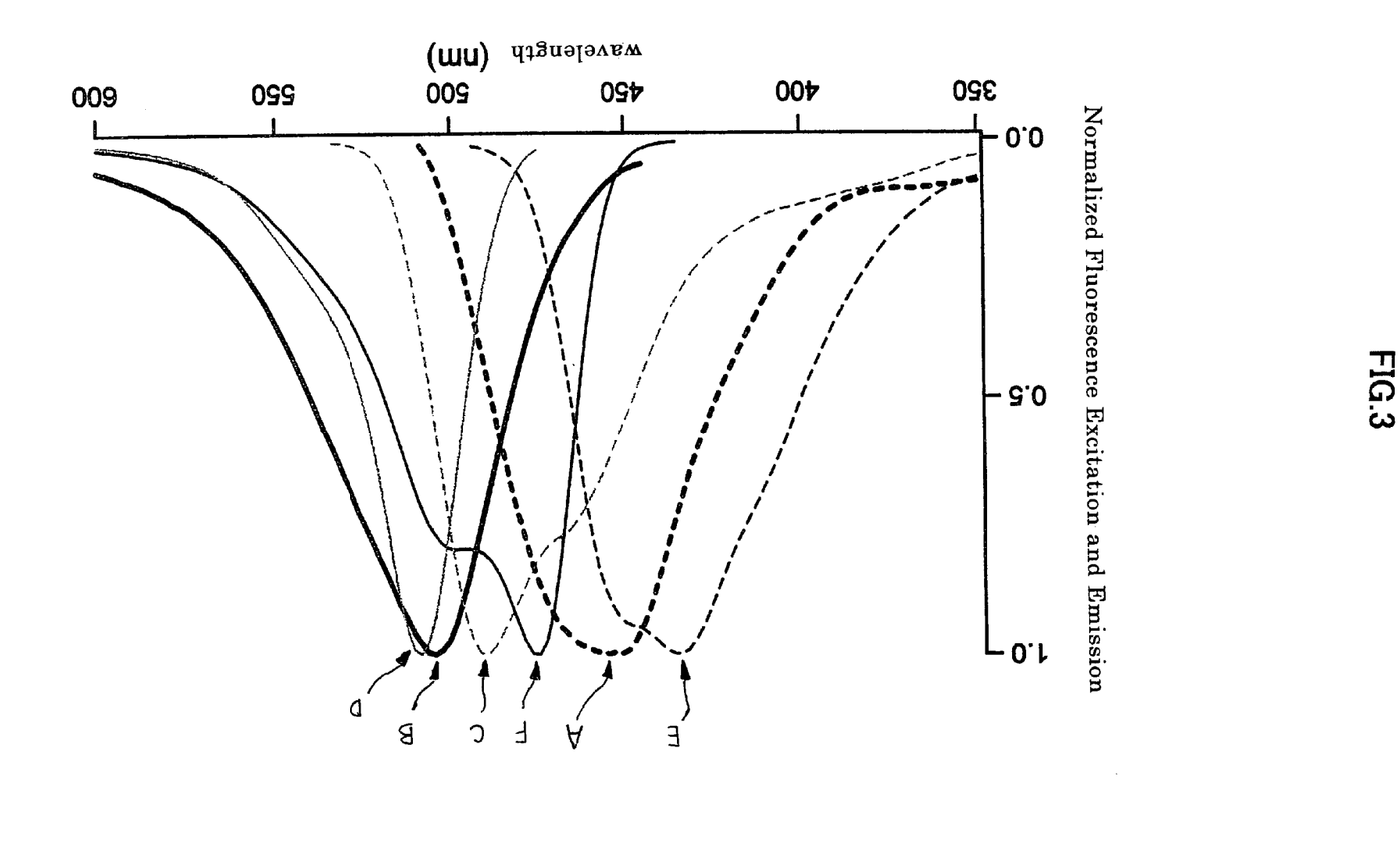
FIG. 3 shows the excitation (broken line) and emission (solid line) spectra of ECFP, ECGFP and EGFP.

The fluorescence excitation and emission spectra of ECGFP are shown together with those of ECFP and EGFP in FIG. 3. In the figure, the fluorescence excitation spectrum of ECGFP is shown by Curve A (broken line) and the emission spectrum of ECGFP by Curve B (solid line). Also, FIG. 3 shows the fluorescence excitation spectrum of EGFP by Curve C (broken line), the emission spectrum of EGFP by Curve D (solid line), the fluorescence excitation spectrum of ECFP by Curve E (broken line) and the emission spectrum of ECFP by Curve F (solid line).

As is seen from FIG. 3, the excitation and emission peaks of ECGFP (455 nm and 506 nm, respectively) were fairly close to those of the long wavelength component of ECFP (452 nm and 505 nm, respectively). This suggests that the π-π interaction favored the quantum state in which the longer wavelength predominated. FIG. 3 also indicates that ECGFP and ECFP have similar emission peaks (ECGFP, 506 nm and ECFP, 511 nm), but that ECGFP exhibits a larger Stokes' shift (the gap in wavelength between excitation and emission peaks). In ECGFP, since it has a larger Stokes' shift than ECFP or EGFP, the fluorescent signal and excitation light can be easily separated in observation of the illuminated fluorescence.

Further, ECGFP, EGFP and ECFP were examined for pH resistance.

Firstly, using any of the following materials were used to prepare a series of pH buffers were prepared such that the pH values fell within the range of 3.8 to 11:50 mM acetate (pH 3.8 to 5.6), $Na_2HPO_4$—$Na_2H_2PO_4$ (pH 5.5 to 7.0), 2-(N-morpho) ethane sulfonate (pH 5.5 to 6.0), 3-(N-morpho) propane sulfonate (pH 6.5 to 7.0), HEPES (pH 7.0 to 7.9), glycine (pH 9.0 to 10.0) and phosphate (pH 11). A solution for examining the pH resistance was prepared by concentrating protein in a weak buffer solution and then mixing said weak buffer solution with a buffer solution at a certain pH in an equivalent amount.

Figure 4:
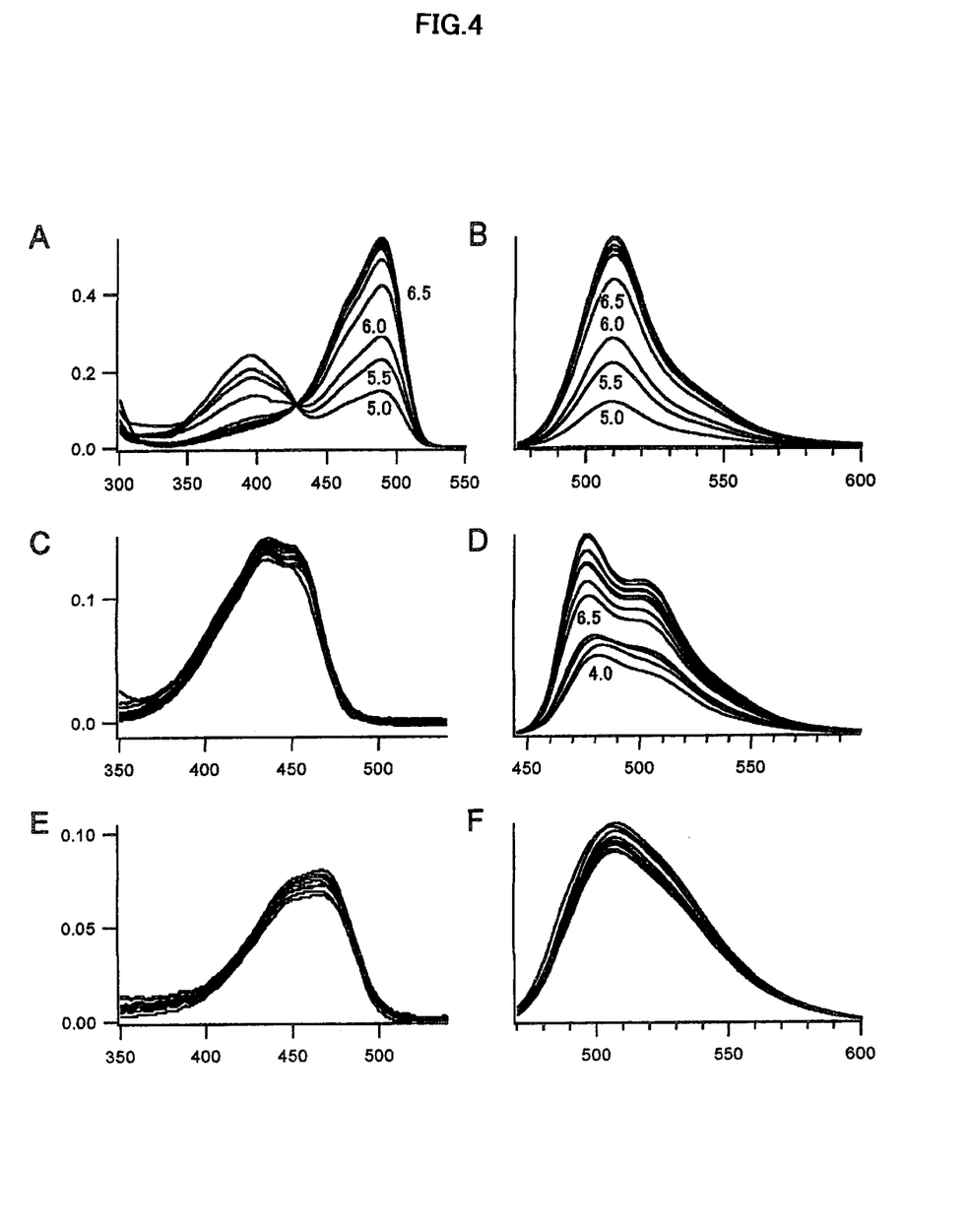
FIG. 4 shows the pH-dependency of the excitation and emission spectra of EGFP, ECFP and ECGFP respectively, where (A): the absorbance spectrum of EGFP, (B): the emission spectrum of EGFP, (C): the absorbance spectrum of ECFP, (D): the emission spectrum of ECFP, (E): the absorbance spectrum of ECGFP, and (F): the emission spectrum of ECGFP.
Figure 5:
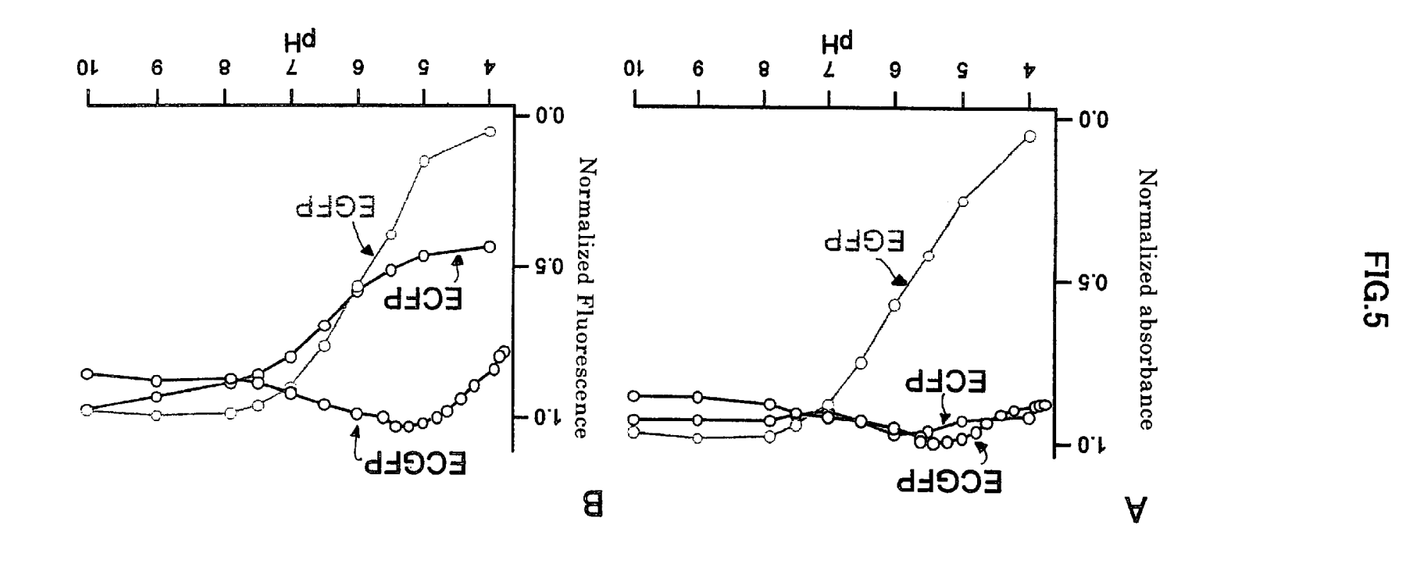
FIG. 5 shows the pH-dependency of the absorbance and emission peaks of EGFP, ECFP and ECGFP respectively. In the figure, (A) illustrates the relationship between the absorbance peak and pH and (B) illustrates the relationship between the fluorescence peak and pH.

The absorbance and emission wavelength spectra measured using the resultant solutions are shown in FIG. 4 and FIG. 5. In FIG. 4, the representation is as follows: (A): the absorbance spectrum of EGFP, (B): the emission spectrum of EGFP, (C): the absorbance spectrum of ECFP, (D): the emission spectrum of ECFP, (E): the absorbance spectrum of ECGFP and (F): the emission spectrum of ECGFP. Further, in FIG. 5, (A) represents the re-plotted spectra of (A), (C) and (E) in FIG. 4, whereas (B) represents the re-plotted spectra of (B), (D) and (F) in FIG. 4.

Moreover, regarding EGFP, ECFP and ECGFP, the quantum yield (Φ) and molar absorbance coefficient (ε) were measured. The values of the quantum yield (Φ) and molar absorbance coefficient (ε) were measured in 50 mM HEPES (pH 7.5). The quantum yield (Φ) of ECGFP was determined by comparison with the standard (fluorescein (Φ=0.91) and ECFP (Φ=0.40)). In order to measure the protein concentration for calculating the molar absorbance coefficient, a Bradford assay kit (Bio Rad) was used, with BSA (bovine serum albumin) as the standard material. The results thereof are shown in Table 1.

TABLE 1

| Designation | mutations | $\lambda_{abs}$ ($\epsilon$) | $\lambda_{em}$ ($\Phi$) | pKa |
|---|---|---|---|---|
| EGFP | F64L, S65T | 488 (55–57) | 507–509 (0.60) | 6 |
| ECFP | F64L, S65T, Y66W, N146I, M153T, V163A, N164H | 434 (33.9) 452 | 476 (0.40) 505 | 4–6 |
| ECGFP | F64L, S65T, Y66W, N146I, M153T, V163A, N164H, T203Y | 463 (23.9) | 506 (0.14) | <4 |

In the above Table 1, λ abs represents the peak of the absorbance spectrum in units of nanometers. ε in parentheses is the molar absorbance coefficient in units of $10^3 M^{-1} cm^{-1}$. λ em represents the peak of the emission spectrum in units of nanometers. Φ in parentheses is the quantum yield. Ka is the acid dissociation constant, obtained with pKa=−$\log_{10}$Ka.pKa was calculated from FIG. 5(B).

Since the absolute brightness is calculated as the product of ε and Φ, FIG. 1 indicates that the absolute brightness of ECGFP is dimmer than those of EGFP and ECFP around neutral pH. It is known that almost all GFP mutants are quenched to some extent by acidic pH.

On the other hand, as clearly seen from FIGS. 4(A) and (B), EGFP showed an acidification-dependent decrease in the absorbance peak at 488 nm and a concomitant increase in the absorbance peak at 398 nm. In EGFP, the emission (511-nm peak) and excitation (488-nm peak) spectra decreased with decreasing pH, but the fluorescence excitation spectrum showed no compensating increase at 398 nm. This indicates that the species absorbing at 398 nm was non-fluorescent. As shown in FIGS. 4(A) and (B), EGFP exhibited a pKa of 6.0 for both its absorbance and emission spectra, indicating that as shown in FIGS. 5(A) and (B), its absorbance is pH-sensitive but its quantum yield is not.

ECFP was less pH-sensitive than EGFP, as shown in FIGS. 4(A) and (B). Even under conditions of lower pH, there was little effect on its absorbance spectrum (FIG. 4(C)) and only its emission spectrum was weakened. This indicates that its quantum yield is lowered by acidity, as seen in FIGS. 5(A) and (B).

By contrast, ECGFP was stable in a wide pH range (pH 4 to 12), as shown in FIGS. 4(E) and (F). In other words, it is found that ECGFP has fluorescence properties that are unchanging under any pH conditions, as seen in FIG. 5(A) and (B).

The fluorescence of ECGFP can be used to accurately report the species of molecules being imaged for the analysis of intracellular membrane dynamics of acidic organelles such as, for example, secretory and endocytosis organelles.

Effect of the Invention

As described in detail above, the method for mutagenesis according to the present invention allows mutations to be introduced simultaneously at multiple sites. To this effect, the method for mutagenesis according to the present invention makes it possible to synthesize a desired base sequence in a rapid and simple manner at low cost. Thus, the present invention provides a new approach in genetic engineering that is widely-applicable.

Sequence Listing Free Text

SEQ ID NO. 5 to 7 represent synthetic primers.

The symbol "n" of the 9th, 10th, or 11th base of SEQ ID NO. 7 represents a, t, c or g.

What is claimed is:

1. A method for mutagenesis comprising:
    annealing one or more primers having a nucleotide sequence containing at least one mutation and a phosphorylated 5'-terminus, to a DNA template;
    elongating the annealed primer or primers by using a DNA polymerase;
    ligating the phosphorylated 5'-terminus and the elongated terminus of the primer or primers by means of a DNA ligase to synthesize a circular DNA containing said primer or primers;
    denaturing the circular DNA;
    repeating the reactions of annealing, elongating, litgating, and denaturing to amplify the circular DNA to generate DNA products including multiple copies of a single-stranded circular DNA containing the primer or primers;
    selectively digesting the DNA products other than the single-stranded circular DNA to produce megaprimer fragments;
    annealing said megaprimer fragments to said single-stranded circular DNA; and
    elongating the annealed megaprimer fragments by using said DNA polymerase to synthesize a double stranded DNA.

2. The method for mutagenesis according to claim 1 wherein said primers are used to introduce mutations at multiple sites simultaneously.

3. The method for mutagenesis according to claim 1, wherein said primers comprise degenerative primers to introduce random mutations at certain sites in a nucleotide sequence.

4. The method for mutagenesis according to claim 1, further comprising:
    before annealing the megaprimer fragments, adding an auxiliary primer complementary to a region adjacent to the nucleotide sequence in which mutations are introduced.

5. The method for mutagenesis according to claim 4 wherein said auxiliary primer is a T7 primer.

6. The method for mutagenesis according to claim 1 further comprising:
    digesting selectively the other DNA products by methylated and hemi-methylated nucleotide sequences are selectively cut.

7. The method for mutagenesis according to claim 1 wherein DpnI is used to selectively digest the DNA products.

8. The method for mutagenesis according to claim 1 wherein in elongating the primer or primers, a thermostable high-fidelity DNA polymerase is used, and in ligating the phosphorylated 5'-terminus and the elongated terminus, a thermostable DNA ligase is used.

9. The method for mutagenesis according to claim 8, wherein the method is conducted in a reaction solution comprising at least said primers, said template DNA, said thermostable high-fidelity DNA polymerase and said thermostable DNA ligase.

10. The method of mutagenesis according to claim 1 wherein the DNA products further comprises: a single-stranded circular DNA without the primer or primers, a single-stranded circular DNA with the primer or primers annealed to the DNA template to form a double-stranded circular DNA, and a single-stranded circular DNA without the primer or primers annealed to the DNA template to form another double-stranded circular DNA.

11. A method for mutagenesis comprising:
- annealing one or more primers having a nucleotide sequence containing at least one mutation and a phosphorylated 5'-terminus, to a DNA template;
- elongating the annealed primer or primers by using a DNA polymerase;
- ligating the phosphorylated 5'-terminus and the elongated terminus of the primer or primers by means of a DNA ligase to synthesize a circular DNA containing said primer or primers;
- denaturing the circular DNA;
- repeating the reactions of annealing, elongating, litgating, and denaturing to amplify the circular DNA to generate DNA products including multiple copies of a single-stranded circular DNA containing the primer or primers;
- selectively digesting the DNA products other than the single-stranded circular DNA to produce megaprimer fragments;
- annealing said megaprimer fragments to said single-stranded circular DNA;
- elongating the annealed megaprimer fragments by using said DNA polymerase to synthesize a double stranded DNA; and
- adding an auxiliary primer complementary to a region adjacent to the nucleotide sequence in which mutations are introduced,
- wherein said auxiliary primer is a T7 primer.

12. A method for mutagenesis comprising:
- annealing one or more primers having a nucleotide sequence containing at least one mutation and a phosphorylated 5'-terminus, to a DNA template;
- elongating the annealed primer or primers by using a DNA polymerase;
- ligating the phosphorylated 5'-terminus and the elongated terminus of the primer or primers by means of a DNA ligase to synthesize a circular DNA containing said primer or primers;
- denaturing the circular DNA;
- repeating the reactions of annealing, elongating, litgating, and denaturing to amplify the circular DNA to generate DNA products including multiple copies of a single-stranded circular DNA containing the primer or primers;
- selectively digesting the DNA products other than the single-stranded circular DNA to produce megaprimer fragments;
- annealing said megaprimer fragments to said single-stranded circular DNA; and
- elongating the annealed megaprimer fragments by using said DNA polymerase to synthesize a double stranded DNA,
- wherein a thermostable high-fidelity DNA polymerase and/or a thermostable DNA ligase are used in synthesizing the single-stranded circular DNA and the double-stranded circular DNA.

* * * * *

SEQUENCE LISTING

<160> NUMBER OF SEQ ID NOS: 9

<210> SEQ ID NO 1
<211> LENGTH: 720
<212> TYPE: DNA
<213> ORGANISM: Aequorea victoria
<220> FEATURE:
<221> NAME/KEY: CDS
<222> LOCATION: (1)...(717)

<400> SEQUENCE: 1

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
 65                  70                  75                  80
```

-continued

| | |
|---|---|
| cag cac gac ttc ttc aag tcc gcc atg ccc gaa ggc tac gtc cag gag<br>Gln His Asp Phe Phe Lys Ser Ala Met Pro Glu Gly Tyr Val Gln Glu<br>             85                  90                  95 | 288 |
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>         100                 105                 110 | 336 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>     115                 120                 125 | 384 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br> 130                 135                 140 | 432 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>145                 150                 155                 160 | 480 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>                 165                 170                 175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>             180                 185                 190 | 576 |
| ccc gtg ctg ctg ccc gac aac cac tac ctg agc acc cag tcc gcc ctg<br>Pro Val Leu Leu Pro Asp Asn His Tyr Leu Ser Thr Gln Ser Ala Leu<br>         195                 200                 205 | 624 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>     210                 215                 220 | 672 |
| gtg acc gcc gcc ggg atc act ctc ggc atg gac gag ctg tac aag<br>Val Thr Ala Ala Gly Ile Thr Leu Gly Met Asp Glu Leu Tyr Lys<br>225                 230                 235 | 717 |
| taa | 720 |

<210> SEQ ID NO 2
<211> LENGTH: 239
<212> TYPE: PRT
<213> ORGANISM: Aequorea victoria

<400> SEQUENCE: 2

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 3
<211> LENGTH: 717
<212> TYPE: DNA
<213> ORGANISM: Aequorea victoria
<220> FEATURE:
<221> NAME/KEY: CDS
<222> LOCATION: (1)...(714)

<400> SEQUENCE: 3 atg agt aaa gga gaa gaa ctt ttc act gga gtt gtc cca att ctt gtt       48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag       96
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tgc      144
Gly Glu Gly Asp Ala Thr Tyr Gly Lys Leu Thr Leu Lys Phe Ile Cys
        35                  40                  45 act act gga aaa cta cct gtt cca tgg cca aca ctt gtc act act ttc      192
Thr Thr Gly Lys Leu Pro Val Pro Trp Pro Thr Leu Val Thr Thr Phe
    50                  55                  60 tct tat ggt gtt caa tgc ttt tca aga tac cca gat cat atg aaa cag      240
Ser Tyr Gly Val Gln Cys Phe Ser Arg Tyr Pro Asp His Met Lys Gln
65                  70                  75                  80 cat gac ttt ttc aag agt gcc atg ccc gaa ggt tat gta cag gaa aga      288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc      336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att      384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac      432
Asp Phe Lys Glu Asp Gly Asn Ile Leu Gly His Lys Leu Glu Tyr Asn
    130                 135                 140 tat aac tca cac aat gta tac atc atg gca gac aaa caa aag aat gga      480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt      528
Ile Lys Val Asn Phe Lys Ile Arg His Asn Ile Glu Asp Gly Ser Val
                165                 170                 175 caa cta gca gac cat tat caa caa aat act cca att ggc gat ggc cct      576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg      624
Val Leu Leu Pro Asp Asn His Tyr Leu Ser Thr Gln Ser Ala Leu Ser
        195                 200                 205
```

```
aaa gat ccc aac gaa aag aga gac cac atg gtc ctt ctt gag ttt gta    672
Lys Asp Pro Asn Glu Lys Arg Asp His Met Val Leu Leu Glu Phe Val
210                 215                 220 aca gct gct ggg att aca cat ggc atg gat gaa cta tac aaa            714
Thr Ala Ala Gly Ile Thr His Gly Met Asp Glu Leu Tyr Lys
225                 230                 235 taa                                                                717

<210> SEQ ID NO 4
<211> LENGTH: 238
<212> TYPE: PRT
<213> ORGANISM: Aequorea victoria

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 27
<212> TYPE: DNA
<213> ORGANISM: Artificial Sequence
<220> FEATURE:
<223> OTHER INFORMATION: Synthetically generated primer

<400> SEQUENCE: 5
gcactgcacg ccccaggtca gggtggt                                      27

<210> SEQ ID NO 6
<211> LENGTH: 26
<212> TYPE: DNA
```

<213> ORGANISM: Artificial Sequence
<220> FEATURE:
<223> OTHER INFORMATION: Synthetically generated primer

<400> SEQUENCE: 6
gggcggactg gtagctcagg tagtgg                                26

<210> SEQ ID NO 7
<211> LENGTH: 21
<212> TYPE: DNA
<213> ORGANISM: Artificial Sequence
<220> FEATURE:
<223> OTHER INFORMATION: Synthetically generated primer
<221> NAME/KEY: misc_feature
<222> LOCATION: 9, 10, 11
<223> OTHER INFORMATION: n = a, t, g, or c
<400> SEQUENCE: 7
gcggactgnn ngctcaggta g                                     21

<210> SEQ ID NO 8
<211> LENGTH: 239
<212> TYPE: PRT
<213> ORGANISM: Aequorea victoria

<400> SEQUENCE: 8

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 9
<211> LENGTH: 239
<212> TYPE: PRT

-continued

```
<213> ORGANISM: Aequorea victoria

<400> SEQUENCE: 9

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```